(12) United States Patent
Duan et al.

(10) Patent No.: US 11,622,749 B2
(45) Date of Patent: Apr. 11, 2023

(54) GASTROINTESTINAL LIQUID BIOPSY SAMPLING DEVICE

(71) Applicant: Ankon Medical Technologies (Shanghai) Co., LTD., Shanghai (CN)

(72) Inventors: Xiaodong Duan, Pleasanton, CA (US); Lei Liu, Suzhou (CN)

(73) Assignee: ANKON MEDICAL TECHNOLOGIES (SHANGHAI) CO., LTD., Shanghai (CN)

(*) Notice: Subject to any disclaimer, the term of this patent is extended or adjusted under 35 U.S.C. 154(b) by 372 days.

(21) Appl. No.: 16/775,718

(22) Filed: Jan. 29, 2020

(65) Prior Publication Data

US 2020/0237349 A1    Jul. 30, 2020

(30) Foreign Application Priority Data

Jan. 29, 2019  (CN) .......................... 201910086588.X

(51) Int. Cl.
*A61B 10/00*    (2006.01)
*A61B 10/04*    (2006.01)

(52) U.S. Cl.
CPC .......... *A61B 10/0045* (2013.01); *A61B 10/04* (2013.01); *A61B 2010/0061* (2013.01)

(58) Field of Classification Search
CPC ................ A61B 10/0045; A61B 10/04; A61B 2010/0061; A61B 5/6861; A61B 90/36; A61B 5/036; A61B 5/038; A61B 5/07; A61B 5/073; A61B 5/42; A61B 5/4839; A61B 2562/0247; A61B 2562/162; A61B 1/041; A61B 10/02; A61B 10/06; A61B 5/062; A61B 1/00004; A61B 1/00016; A61B 1/0002; A61B 5/0084; A61B 5/053; A61B 5/14539; A61B 5/14546
See application file for complete search history.

(56) References Cited

U.S. PATENT DOCUMENTS

| | | | | |
|---|---|---|---|---|
| 4,481,952 | A * | 11/1984 | Pawelec | A61B 10/00 600/593 |
| 2011/0245611 | A1 * | 10/2011 | Yeh | A61B 1/041 600/118 |
| 2013/0276665 | A1 * | 10/2013 | Dalrymple | B61B 13/122 104/23.1 |
| 2013/0337030 | A1 * | 12/2013 | Adam | A23K 10/26 426/531 |
| 2019/0175110 | A1 * | 6/2019 | Gregersen | A61B 5/14539 |
| 2020/0138416 | A1 * | 5/2020 | Shalon | A61B 10/0045 |

* cited by examiner

*Primary Examiner* — Kaylee R Wilson
*Assistant Examiner* — Raymond P Dulman
(74) *Attorney, Agent, or Firm* — Treasure IP Group, LLC

(57) ABSTRACT

The present invention provides a gastrointestinal liquid biopsy sampling device. The sampling device includes an enclosure and expandable materials. The enclosure includes through holes cut in the wall of the enclosure, and targeted dissolution membranes covering the through holes that can be dissolved at targeted regions. The expandable materials are arranged at the positions corresponding to the through holes. The expandable materials expand after absorbing liquid and close the through holes.

8 Claims, 5 Drawing Sheets

GASTROINTESTINAL LIQUID BIOPSY SAMPLING DEVICE

CROSS-REFERENCE OF RELATED APPLICATIONS

The application claims priority to Chinese Patent Application No. 201910086588.X filed on Jan. 29, 2019, the contents of which are incorporated by reference herein.

FIELD OF INVENTION

The present invention relates to a medical device, and more particularly to a gastrointestinal liquid biopsy sampling device.

BACKGROUND

Gastrointestinal biopsy technique is of great significance for the diagnosis of gastrointestinal disorders. Traditional gastrointestinal biopsy technique refers to using tissue clamps, electrosurgical tools, and puncture needles to obtain liquid for biopsy or diseased tissues with the assistance of endoscopy. For example, under endoscopy, tissue clamps directly obtain diseased tissues, and endoscopic mucosal resection/endoscopic submucosal dissection (EMR/ESD) and endoscopic ultrasound fine needle aspiration (EUS-FNA), etc. This biopsy method brings great pain to the patient. It is demanding for the operating skills of physician and is accompanied by risks such as bleeding, artificial ulcers, tissue fibrosis, and perforation of mucosa.

With the development of micro-machining technology, micro-electromechanical technology (MEMS) represented by capsule endoscopy has opened up a new way for minimally invasive/comfortable biopsy sampling of digestive tract. However, these techniques still face problems such as high cost, complex energy supply equipment, and insufficient positioning accuracy in the process of gastrointestinal biopsy.

SUMMARY OF THE INVENTION

The present invention provides a gastrointestinal liquid biopsy sampling device. The gastrointestinal liquid biopsy sampling device can accurately sample liquid at a targeted region without an external power source, and can protect the sampled liquid from being contaminated by the liquid at other regions.

The present invention provides a gastrointestinal liquid biopsy sampling device, comprising: an enclosure, wherein the enclosure comprises through holes cut in the wall of the enclosure, and targeted dissolution membranes covering the through holes that dissolve at targeted regions; and expandable materials, arranged at the positions corresponding to the through holes, wherein the expandable materials expand after absorbing liquid and close the through holes.

Further, the enclosure is in a shape of capsule.

Further, the enclosure comprises a water absorbing material.

Further, the expandable materials expand after absorbing liquid to block the through holes, so that the through holes are closed.

Further, the enclosure further comprises piston rings, and the piston rings comprise flow passages for liquid to flow through the piston rings, wherein each piston ring is configured with its outer wall against the inner wall of the enclosure, the expandable materials are disposed at a side of the piston ring away from the through holes, and after absorbing liquid, the expandable materials expand to push the piston rings to block the through holes.

Further, the expandable materials are granular, and the granular expandable materials are disposed on the water absorbing material or the inner wall of the enclosure.

Further, the expandable materials are water absorbing materials, and the enclosure further comprises piston rings, and the piston rings comprise flow passages for liquid to flow through the piston rings, wherein each piston ring is configured with its outer wall against the inner wall of the enclosure, the water absorbing materials are disposed at a side of the piston ring away from the through holes, and after absorbing liquid, the water absorbing materials expand to push the piston rings to block the through holes.

Further, the enclosure further comprises balance weights disposed inside.

Further, the enclosure is capsule-shaped, comprising a body and two ends on both sides of the body, and the through holes are on the body and/or one or two ends.

Further, the enclosure further comprises tracer particles inside to display the position of the gastrointestinal liquid biopsy sampling device in the digestive tract through medical imaging technique.

In summary, the present invention provides an enclosure with through holes cut in its wall and targeted dissolution membranes covering the through holes. The targeted dissolution membranes can be dissolved at a targeted region, that is, when the gastrointestinal liquid biopsy sampling device reaches a targeted region in the digestive tract, such as the stomach, duodenum, jejunum or colon, etc., the targeted dissolution membranes can be dissolved due to the special environment of the targeted region, such as pH value, special flora and/or specific enzyme, so that the liquid at the targeted region can enter the enclosure through the through holes. Therefore, the gastrointestinal liquid biopsy sampling device can accurately sample liquid from a targeted region of the digestive tract without an external power source. Further, when the liquid at a targeted region enters the enclosure through the through holes, a part of the liquid can be absorbed by the expandable materials. After absorbing liquid, the expandable materials expand and close the through holes, so that outside liquid can no longer enter the enclosure. Therefore, the gastrointestinal liquid biopsy sampling device can protect the sampled liquid from being contaminated by the liquid at other regions. Further, the present invention provides a water absorbing material that is arranged for a relatively smooth sampling of liquid, tracer particles that are arranged for display of the position of the sampling device in the human body, and balance weights that are arranged for an easy immersion of the sampling device in the liquid to be sampled.

The above description is only an overview of the technical solutions of the invention. For a thorough understanding of the technical means of the invention, and implementation in accordance with the specification, and that the above-described and other objects, features and advantages of the invention can be more clearly understood, detailed description of the preferred embodiments can be described in detail with reference to the accompanying drawings.

DETAILED DESCRIPTION

The present invention can be described in detail below with reference to the accompanying drawings and preferred embodiments.

The present invention provides a gastrointestinal liquid biopsy sampling device. The gastrointestinal liquid biopsy sampling device can accurately sample liquid at a targeted region without an external power source, and can protect the sampled liquid from being contaminated by the liquid at other regions.

Figure 1:
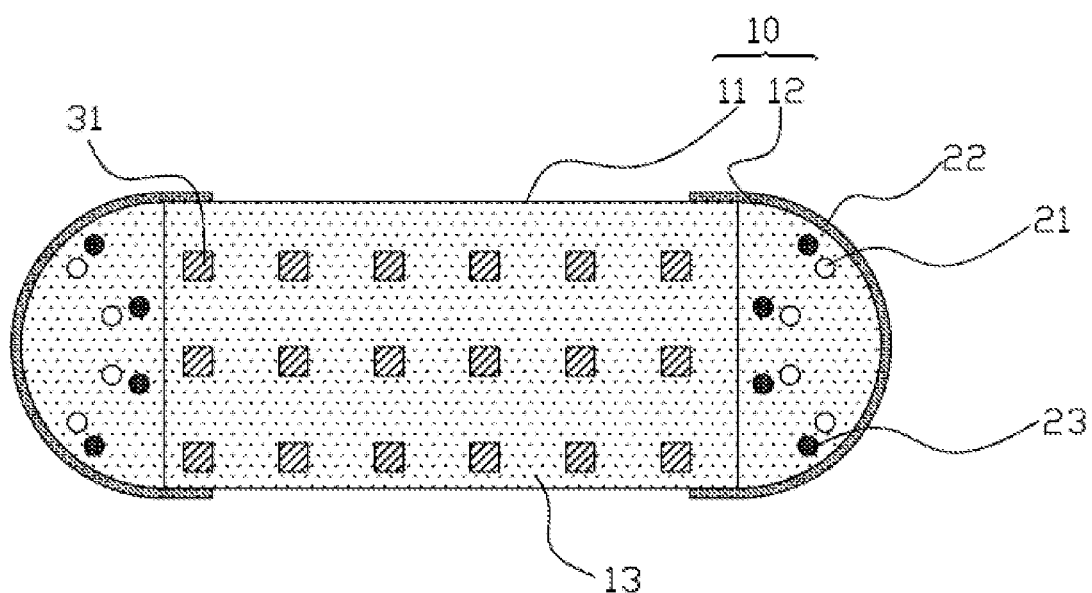
FIG. 1 shows a structural view of a gastrointestinal liquid biopsy sampling device according to the first embodiment of the invention.
Figure 2:
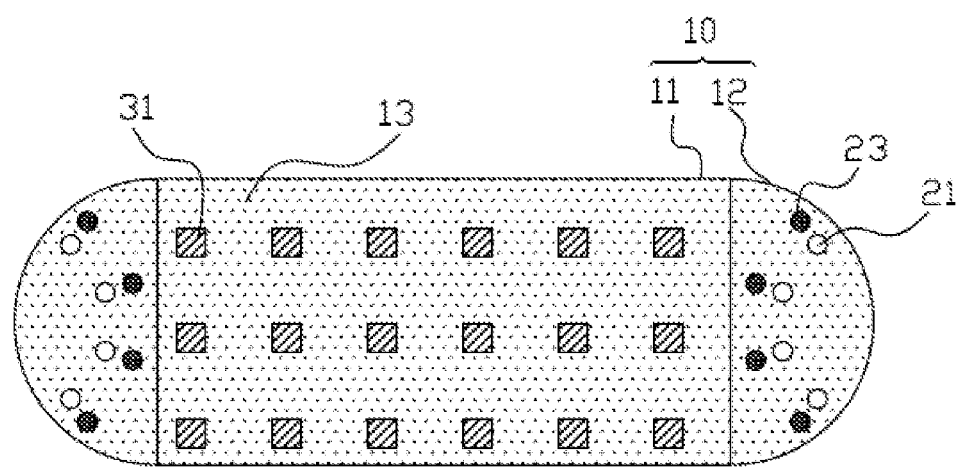
FIG. 2 shows a structural view of the gastrointestinal liquid biopsy sampling device of FIG. 1 after targeted dissolution membranes are dissolved.
Figure 3:
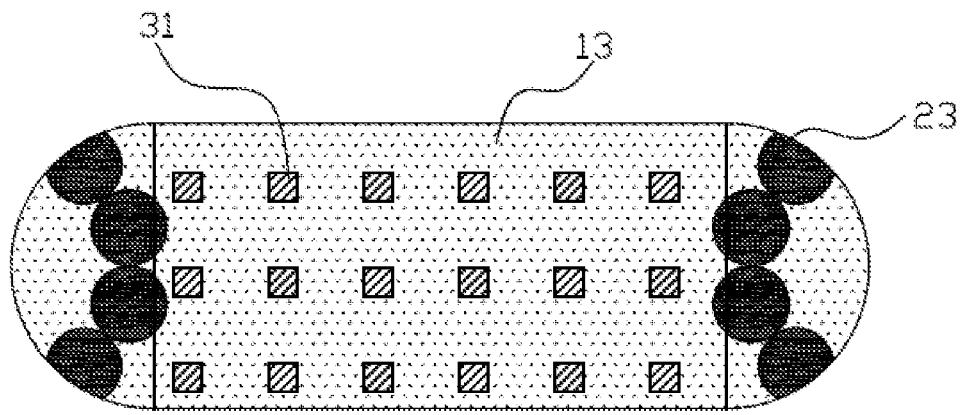
FIG. 3 shows a structural view of the gastrointestinal liquid biopsy sampling device of FIG. 1 after sampling is completed.

FIG. 1 shows a structural view of the gastrointestinal liquid biopsy sampling device according to the first embodiment of the invention. FIG. 2 shows a structural view of the gastrointestinal liquid biopsy sampling device of FIG. 1 after targeted dissolution membranes are dissolved. FIG. 3 shows a structural view of the gastrointestinal liquid biopsy sampling device of FIG. 1 after sampling is completed. Referring to FIGS. 1~3, the gastrointestinal liquid biopsy sampling device according to the first embodiment of the present invention comprises an enclosure 10, through holes 21 cut in the wall of the enclosure 10, targeted dissolution membranes 22 covering the through holes 21 that can be dissolved at targeted regions. The gastrointestinal liquid biopsy sampling device further comprises expandable materials 23, arranged at the positions corresponding to the through holes 21, wherein the expandable materials 23 expand after absorbing liquid and close the through holes 21.

In the embodiment, the present invention provides an enclosure 10 with through holes 21 cut in its wall and targeted dissolution membranes 22 covering the through holes 21. The targeted dissolution membranes 22 can be dissolved at a targeted region, that is, when the gastrointestinal liquid biopsy sampling device reaches a targeted region in GI tract, such as the stomach, duodenum, jejunum or colon, etc., the targeted dissolution membranes can be dissolved (see FIG. 2) due to the special environment of the targeted region, such as pH value, special flora and/or specific enzyme, so that the liquid at the targeted region can enter the enclosure 10 through the through holes 21. Therefore, the gastrointestinal liquid biopsy sampling device can accurately sample liquid from a targeted region of the digestive tract without an external power source. Further, when the liquid at a targeted region enters the enclosure 10 through the through holes 21, a part of the liquid can be absorbed by the expandable materials 23. After absorbing liquid, the expandable materials 23 expand (see FIG. 3) and close the through holes 21, so that outside liquid can no longer enter the enclosure. After liquid sampling is completed, the sampling device can be expelled from the digestive tract, and the sampled liquid can be tested. Therefore, the gastrointestinal liquid biopsy sampling device can protect the sampled liquid from being contaminated by the liquid at other regions.

In the embodiment, the enclosure 10 can be made of materials such as medical grade polycarbonate, polyurethane, polyacrylate, polymethyl methacrylate, polyetheretherketone, polystyrene, or polyethylene. In the embodiment, in order to facilitate the movement of the sampling device in the digestive tract, the enclosure 10 can be in a shape of capsule. The capsule-shaped enclosure 10 comprises a body 11 and two ends 12 on both sides of the body 11. In the embodiment, the through holes 21 can be disposed on the two ends 12 of the enclosure 10.

In the embodiment, in order to improve sampling of liquid, the enclosure 10 further comprises a water absorbing material 13 inside. The water absorbing material 13 can be medical polyvinyl alcohol (PVA) sponge, polyurethane (PU) sponge, cotton fiber sponge, lignocellulose sponge, and/or chitosan sponge.

In the embodiment, the expandable materials 23 can be granular, and the granular expandable materials 23 are disposed on the water absorbing material 13 or the inner wall of the enclosure 10, at corresponding positions to the through holes 21. After the expandable materials 23 absorb liquid and expand, the through holes 21 can be blocked. The expansion rate of the expandable materials 23 can be determined according to the actual situation to ensure that sufficient liquid enters the sampling device at a targeted region, and at the same time, ensure that the expandable materials 23 can close the through holes 21 before the sampling device leaves the targeted region.

The expandable materials 23 can be a sodium polyacrylate-modified lignocellulose, a chitosan-modified lignocellulose, or a polymer compounded by a rubber polymer and a water-absorbing resin.

In the embodiment, the targeted dissolution membranes 22 can cover the through holes 21 from the outside of the enclosure 10 or the inside of the enclosure 10 to isolate the communication between the inside and outside of the enclosure 10 in a state that the membranes are not dissolved yet. The material of the targeted dissolution membranes 22 that dissolve at a targeted region can be determined according to the targeted region. For example, when stomach is the targeted region, the targeted dissolution membranes 22 dissolve in stomach, and the material of the targeted dissolution membranes 22 can be EUDRAGIT E100. When duodenum is the targeted region, the targeted dissolution membranes 22 can resist the erosion of acidic liquid in the stomach and dissolve in the duodenum due to high pH to release the drug, for example, the material of the targeted dissolution membranes 22 can be a mixture of EUDRAGIT L100-55 and EUDRAGIT Plastoid B. When colon is the targeted region, the targeted dissolution membranes 22 can be dissolved due to the glycosidases and glycanase produced by special flora in colon to release the drug, for example, the material of the targeted dissolution membranes 22 can be pectin and/or guar gum. In another embodiment, when colon is the targeted region, the targeted dissolution membranes 22 can be dissolved in the colon due to high pH to release the drug, for example, the material of the targeted dissolution membranes 22 can be a mixture of EUDRAGIT S100 and EUDRAGIT Plastoid B. In this embodiment, in order to ensure that the targeted dissolution membranes 22 of the gastrointestinal liquid biopsy sampling device can be dissolved at the targeted region, the thickness of the targeted dissolution membranes 22 can be 100 nm-100 μm.

In one embodiment, the enclosure 10 further comprises tracer particles 31 inside. The tracer particles 31 can display the position of the sampling device in digestive tract under X-ray or magnetic field scanning. The tracer particles 31 can be barium sulfate particles or magnetic metal particles, and the tracer particles 31 have anti-corrosion coatings such as medical polyurethane coating or parylene coating, to prevent the liquid in digestive tract from corroding the tracer particles 31. In the embodiment, to facilitate the fixation of the tracer particles 31, the tracer particles 31 can be fixed in the water absorbing material 13.

Figure 4:
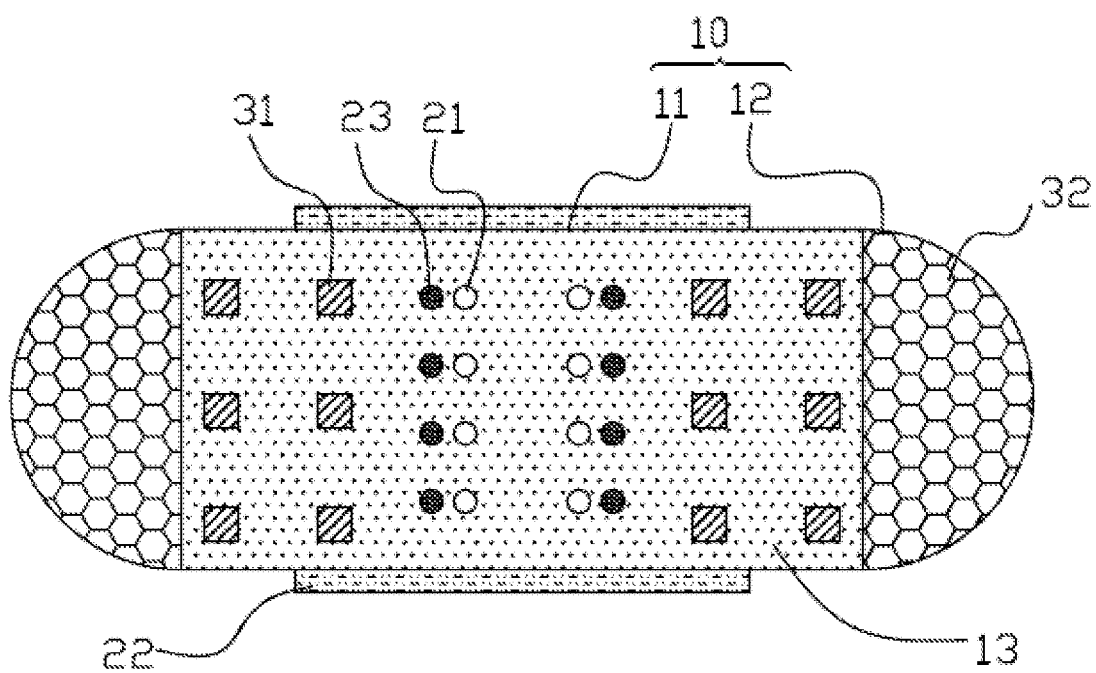
FIG. 4 shows a structural view of the gastrointestinal liquid biopsy sampling device according to the second embodiment of the invention.
Figure 5:
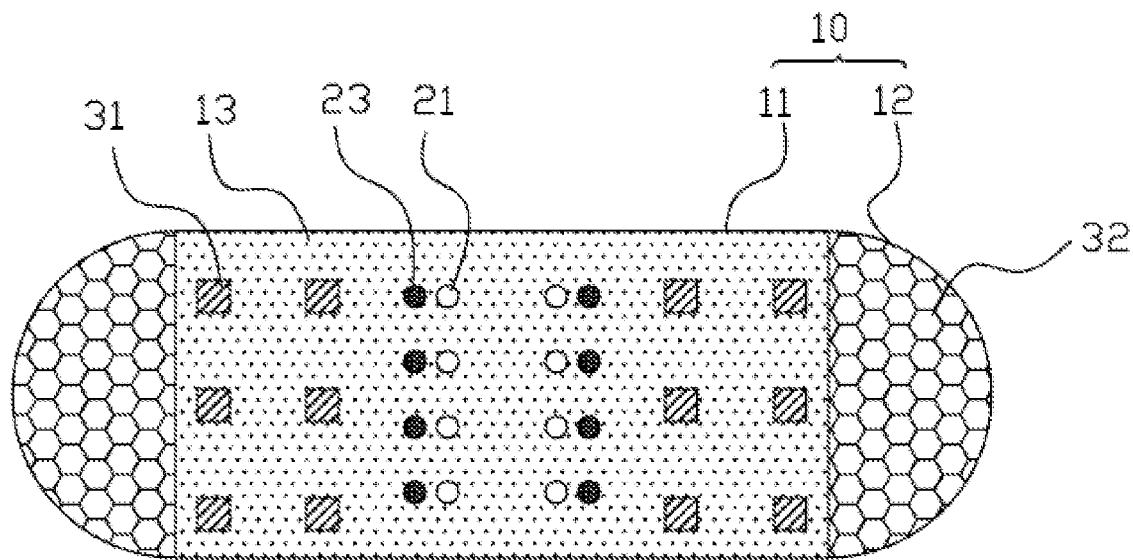
FIG. 5 shows a structural view of the gastrointestinal liquid biopsy sampling device of FIG. 4 after targeted dissolution membranes are dissolved.
Figure 6:
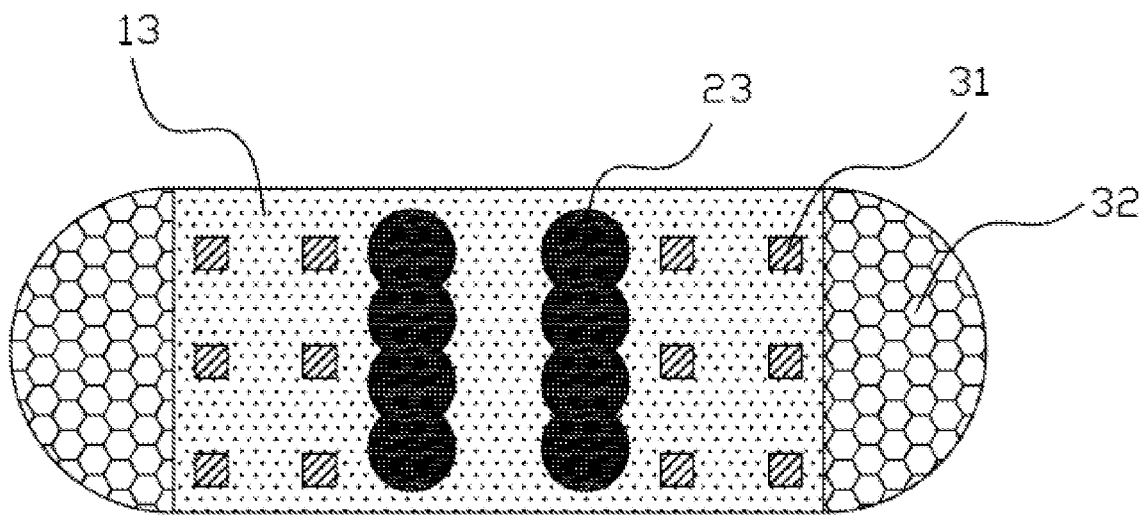
FIG. 6 shows a structural view of the gastrointestinal liquid biopsy sampling device of FIG. 4 after sampling is completed.

FIG. 4 shows a structural view of the gastrointestinal liquid biopsy sampling device according to the second embodiment of the invention. FIG. 5 shows a structural view of the gastrointestinal liquid biopsy sampling device of FIG. 4 after targeted dissolution membranes 22 are dissolved. FIG. 6 shows a structural view of the gastrointestinal liquid biopsy sampling device of FIG. 4 after sampling is completed. Referring to FIGS. 4~6, the gastrointestinal liquid biopsy sampling device according to the second embodiment of the invention is basically the same as the gastrointestinal liquid biopsy sampling device according to the first embodiment of the invention. The difference is that, in the embodiment, the through holes 21 are located in the middle of the enclosure 10, that is, the through holes 21 are located in the body 11 of the capsule-shaped enclosure 10. In other embodiments, the through holes 21 can be disposed on both the body 11 and one or two ends 12 of the capsule-shaped enclosure 10.

Figure 9:
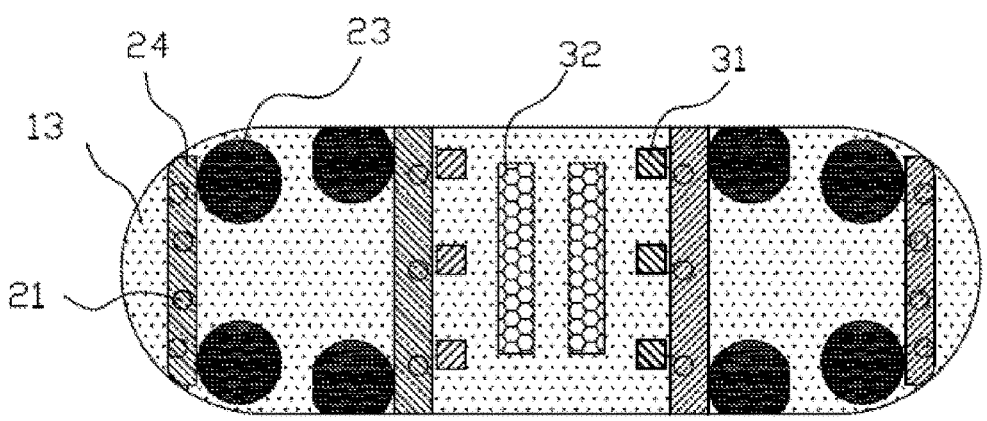
FIG. 9 shows a structural view of the gastrointestinal liquid biopsy sampling device of FIG. 7 after sampling is completed.

Further, in the embodiment, to enable the sampling device to be immersed in the liquid in digestive tract for easy sampling of liquid, the gastrointestinal liquid biopsy sampling device further comprises balance weights 32. The balance weights 32 can be metal blocks such as iron block and also have anti-corrosion coatings such as medical polyurethane coating or parylene coating. The balance weights 32 can be arranged in the two ends 12 as shown in FIG. 4, FIG. 5, or FIG. 6, and can also be arranged in the body 11 as shown in FIG. 7 or FIG. 9.

Figure 7:
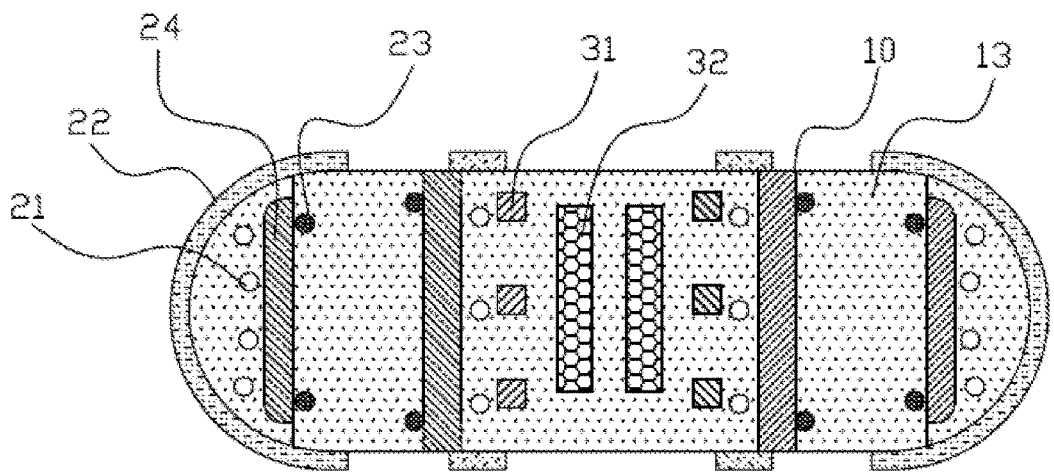
FIG. 7 shows a structural view of the gastrointestinal liquid biopsy sampling device according to the third embodiment of the invention.
Figure 8:
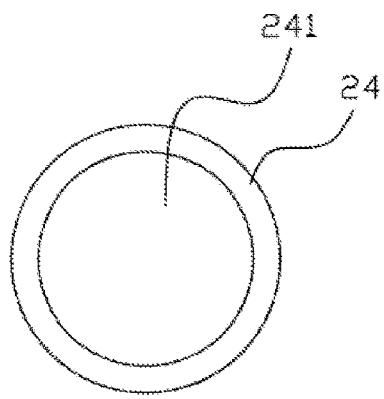
FIG. 8 shows a structural view of a piston ring.

FIG. 7 shows a structural view of the gastrointestinal liquid biopsy sampling device according to the third embodiment of the invention. FIG. 8 shows a structural view of a piston ring. FIG. 9 shows a structural view of the gastrointestinal liquid biopsy sampling device of FIG. 7 after sampling is completed. Referring to FIGS. 7~9, the gastrointestinal liquid biopsy sampling device according to the third embodiment of the invention is basically the same as the gastrointestinal liquid biopsy sampling device according to the second embodiment of the invention. The difference is that in the embodiment, the gastrointestinal liquid biopsy sampling device further comprises piston rings 24, and a flow passage 241 is formed for liquid to flow through the piston ring 24. Each piston ring 24 is configured with its outer wall against the inner wall of the enclosure 10, the expandable materials 23 are disposed at a side of the piston ring 24 away from the through holes 21, and after absorbing liquid, the expandable materials 23 expand to push the piston ring 24 to block the through holes 21.

Figure 10:
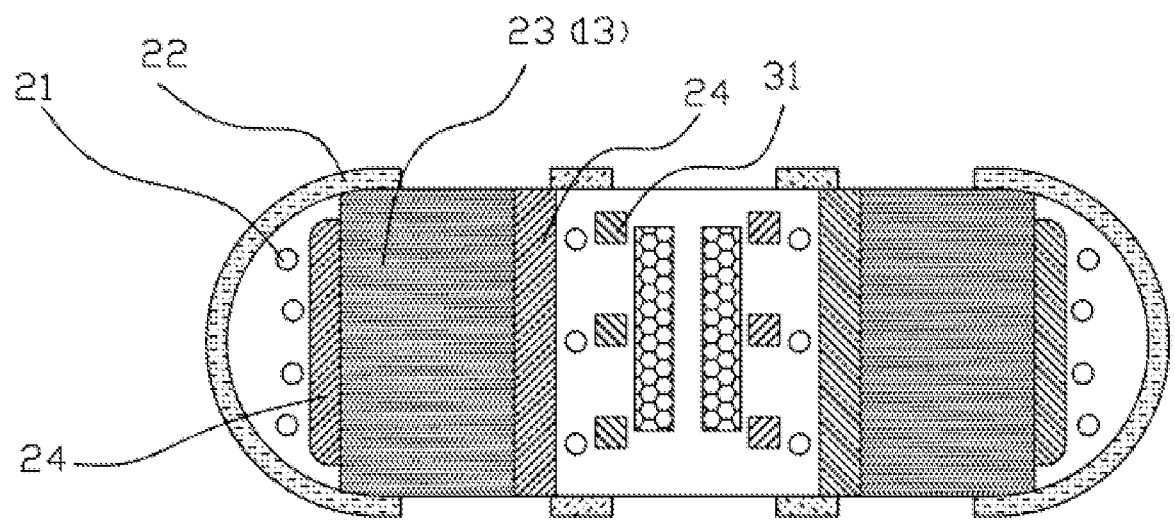
FIG. 10 shows a structural view of the gastrointestinal liquid biopsy sampling device according to the fourth embodiment of the invention.
Figure 11:
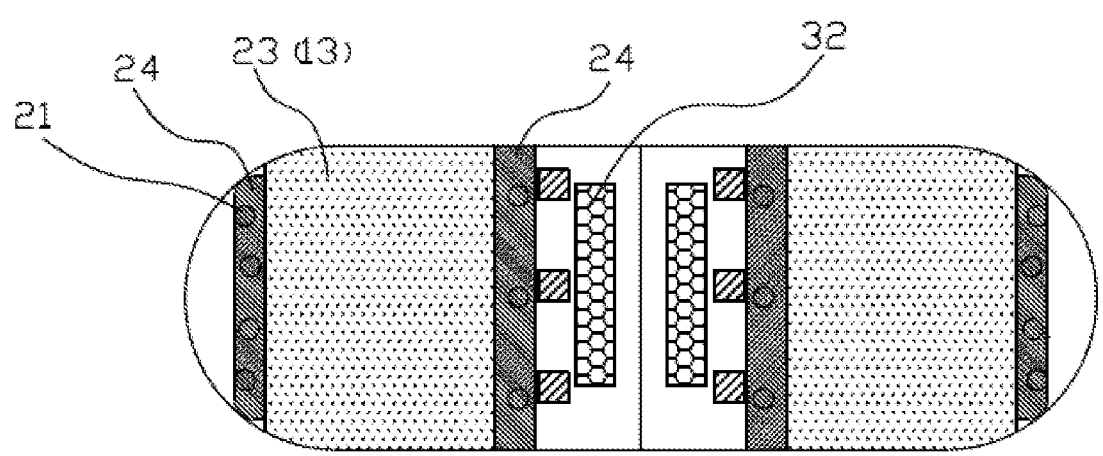
FIG. 11 shows a structural view of the gastrointestinal liquid biopsy sampling device of FIG. 10 after sampling is completed.

FIG. 10 shows a structural view of the gastrointestinal liquid biopsy sampling device according to the fourth embodiment of the invention. FIG. 11 shows a structural view of the gastrointestinal liquid biopsy sampling device of FIG. 10 after sampling is completed. Referring to FIGS. 10~11, the gastrointestinal liquid biopsy sampling device according to the fourth embodiment of the invention is basically the same as the gastrointestinal liquid biopsy sampling device according to the third embodiment of the invention. The difference is that in the embodiment, granular expandable materials 23 are not arranged, and the water absorbing materials 13 are disposed at a side of the piston rings 24 away from the through holes 21. After absorbing liquid, the water absorbing materials 13 expand to push the piston rings 24 to block the through holes 21. That is, in the embodiment, the water absorbing materials 13 are expandable materials 23, and the water absorbing materials 13 are designed to maintain liquid and push the piston rings 24. Preferably, in the embodiment, before absorbing liquid, the water absorbing materials 13 can be in a compressed state.

In summary, the present invention provides an enclosure 10 with through holes 21 cut in its wall and targeted dissolution membranes 22 covering the through holes 21. The targeted dissolution membranes 22 can be dissolved at a targeted region, that is, when the gastrointestinal liquid biopsy sampling device reaches a targeted region in the digestive tract, such as the stomach, duodenum, jejunum or colon, etc., the targeted dissolution membranes 22 can be dissolved due to the special environment of the targeted region (see FIG. 2), such as pH value, special flora and/or specific enzyme, so that the liquid at the targeted region can enter the enclosure 10 through the through holes 21. Therefore, the gastrointestinal liquid biopsy sampling device can accurately sample liquid from a targeted region of the digestive tract without an external power source. Further, when the liquid at a targeted region enters the enclosure 10 through the through holes 21, a part of the liquid can be absorbed by the expandable materials 23. After absorbing liquid, the expandable materials 23 expand (see FIG. 3) and close the through holes, so that outside liquid can no longer enter the enclosure 10. Therefore, the gastrointestinal liquid biopsy sampling device can protect the sampled liquid from being contaminated by the liquid at other regions. Further, the present invention provides a water absorbing material 13 that is arranged for a relatively smooth sampling of liquid, tracer particles 31 that are arranged for display of the position of the sampling device in the human body, and balance weights 32 that are arranged for an easy immersion of the sampling device in the liquid to be sampled.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in particular the matters of shape, size and arrangement of parts within the principles of the present disclosure, up to and including the full extent established by the broad general meaning of the terms used in the claims.

What is claimed is:

1. A gastrointestinal liquid biopsy sampling device, comprising:
an enclosure, including a longitudinal body and two half dome shaped ends, wherein the enclosure comprises through holes cut in a wall of the enclosure, and targeted dissolution membranes covering the through holes that dissolve at targeted regions, wherein the through holes are distributed across the longitudinal body and two half dome shaped ends;

a liquid absorbing material configured to absorb the liquid at the targeted regions, wherein the liquid absorbing material includes expandable materials;

a plurality of piston rings, distributed within the enclosure, each comprising flow passages for the liquid to flow through the piston rings, one piston ring is positioned near each of the half dome shaped ends and one piston ring is positioned between the two half dome shaped ends and along the longitudinal body;

wherein each of the piston rings is provided with its outer wall against an inner wall of the enclosure, the expandable materials are disposed at a side of each of the piston rings away from the through holes and are configured to expand upon absorbing the liquid to push the piston rings to block the through holes; and the expandable materials are configured to push respective piston rings of the two piston rings near the two ends in opposite directions.

2. The gastrointestinal liquid biopsy sampling device of claim 1, wherein the expandable materials are granular, and the granular expandable materials are disposed on the liquid absorbing material or the inner wall of the enclosure.

3. The gastrointestinal liquid biopsy sampling device of claim 1, wherein the liquid absorbing material is medical PVA sponge, PU sponge, cotton fiber sponge, lignocellulose sponge, and/or chitosan sponge.

4. The gastrointestinal liquid biopsy sampling device of claim 1, wherein the expandable materials are the liquid absorbing materials.

5. The gastrointestinal liquid biopsy sampling device of claim 1, wherein the gastrointestinal liquid biopsy sampling device further comprises balance weights disposed inside the enclosure.

6. The gastrointestinal liquid biopsy sampling device of claim 1, wherein the enclosure further comprises tracer particles inside to display a position of the gastrointestinal liquid biopsy sampling device in a digestive tract through a medical imaging technique.

7. The gastrointestinal liquid biopsy sampling device of claim 1, wherein the expandable material is a sodium polyacrylate-modified lignocellulose, a chitosan-modified lignocellulose, or a polymer compounded by a rubber polymer and a water-absorbing resin.

8. The gastrointestinal liquid biopsy sampling device of claim 1, wherein the targeted dissolution membranes are EUDRAGIT E100, a mixture of EUDRAGIT L100-55 and EUDRAGIT Plastoid B, pectin, guar gum, or a mixture of EUDRAGIT S100 and EUDRAGIT Plastoid B.

* * * * *